United States Patent [19]
Glaeser et al.

[11] Patent Number: 4,866,194
[45] Date of Patent: Sep. 12, 1989

[54] METHOD FOR AMMOXIDATION OF PARAFFINS AND CATALYST SYSTEM THEREFOR

[75] Inventors: Linda C. Glaeser, Lyndhurst; James F. Brazdil, Jr., Mayfield Village; Mark A. Toft, Lakewood, all of Ohio

[73] Assignee: The Standard Oil Company, Cleveland, Ohio

[21] Appl. No.: 270,856

[22] Filed: Nov. 14, 1988

Related U.S. Application Data

[62] Division of Ser. No. 200,325, May 31, 1988.

[51] Int. Cl.$^4$ ............................................. C07C 120/14
[52] U.S. Cl. ..................................................... 558/319
[58] Field of Search ......................................... 558/319

[56] References Cited

U.S. PATENT DOCUMENTS 4,801,568  1/1989  Brazdil, Jr. et al. ................. 502/209

*Primary Examiner*—Joseph Paul Brust
*Attorney, Agent, or Firm*—Lynch. C. S.; D. J. Untener; L. W. Evans

[57] ABSTRACT

Disclosed is ammoxidation of $C_3$ to $C_5$ acyclic alkanes with $NH_3$ and $O_2$ using (1) a mole ratio of alkane:$NH_3$ in the range from 2 to 16 and a mole ratio of alkane:$O_2$ in the range 1 to 10 and (2) a mixture of particulate catalyst compositions, the first being especially effective to promote formation of an unsaturated nitrile and an olefin from the paraffin, and the second catalyst composition being especially effective to promote the conversion of the olefin to the unsaturated mononitrile. Catalyst compositions useful in the process are also disclosed.

10 Claims, No Drawings

METHOD FOR AMMOXIDATION OF PARAFFINS AND CATALYST SYSTEM THEREFOR

This a division of co-pending application Ser. No. 200,325, pending, filed May 31, 1988

This invention relates to an improved process for the catalytic ammoxidation of paraffins containing from 3 to 5 carbon atoms to $\alpha$, $\beta$-unsaturated mononitriles, especially paraffins containing 3 to 4 carbon atoms. Most important is the ammoxidation of isobutane to methacrylonitrile and, especially, of propane to acrylonitrile.

Because of the price differential between propylene and propane an economic incentive exists for the development of a viable catalytic process for conversion of propane to acrylonitrile.

Earlier attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated mononitriles.

It is a further object of the invention to provide new catalyst systems for such process.

Still another object is to provide an improved catalytic ammoxidation process for making unsaturated mononitriles from lower paraffins without the use of halogen promoters.

Other objects, as well as aspects, features and advantages, of the present invention will become apparent from a study of the accompanying disclosure and the claims.

The foregoing and other objects of the present invention are achieved by the process of the present invention. There are two main features of the present process invention. The first of these is the use of an excess of the alkane feed with relation to $NH_3$ and molecular oxygen. The second feature, which is used in combination with the high ratio of the $C_3$ to $C_5$ paraffin to $NH_3$ and $O_2$, is that a combination, i.e., a mixture, of catalysts is employed, the first catalyst composition being especially effective to promote formation of an unsaturated mononitrile and an olefin from the paraffin, and the second catalyst composition being especially effective to promote the conversion of the olefin to the unsaturated nitrile. Such mixture is the subject of the composition claims herein.

In the present application "paraffin" designates an acyclic paraffin.

British patent specifications Nos. 1,336,135 and 1,336,136 disclose the use of high ratios of propane or isobutane to ammonia and oxygen, but only single ammoxidation catalysts are used, and the yields of acrylonitrile are extremely poor. U.S. Pat. No. 3,860,534 also discloses use of such high ratios, using a catalyst containing only V and Sb oxides. However, after the catalyst is calcined, it is washed for 24 hours with water and dried, a laborious procedure. A. N. Shatalova et al, in Neftekhiniya 8, No. 4,609–612 (1968), describe the reaction of propane with oxygen and ammonia using a large excess of propane and a mixture of two catalysts, one of which is described as oxides of metals having dehydrogenating characteristics at 550° and 600° C. At 500° C. little or no acrylonitrile was produced. Rather large amounts of propionitrile and acrolein were made per mole of acrylonitrile produced. The per pass conversion of propane to acrylonitrile was generally 2–4 percent with selectivity to acrylonitrile being from 12 to 33 percent.

In the present process when applied to propane ammoxidation a small amount of propylene is produced in relation to the unreacted propane in the effluent. Such propane effluent containing propylene in the amount of up to 8 mole percent, but usually no more than 6 mole percent, of the amount of propane plus propylene can comprise the substrate feed to the present process. And in general the $C_3$ to $C_5$ alkane feed to the process can contain one or more $C_3$ to $C_5$ olefins. The $C_3$ to $C_5$ olefin content of the feed to the present ammoxidation process can contain from zero to 8 mole percent of such olefin(s), based on the moles of $C_3$ to $C_5$ paraffin plus olefins fed, and this feed can be from any source. Although larger amounts of $C_3$ to $C_5$ olefins may be present in the substrate paraffin feed, usual amounts are as stated, and the usual olefin is that corresponding to the particular paraffin fed to the reaction zone of the present process.

According to one aspect of the present invention there is provided a process for the ammoxidation of a $C_3$ to $C_5$ paraffin to an $\alpha$, $\beta$-unsaturated mononitrile which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:$NH_3$ in the range from 2 to 16 (usually 3–7), and a mole ratio of paraffin to $O_2$ in the range from 1 to 10 (usually 1.5–5), said first catalyst composition being 0–99 weight percent of a diluent/support and 100–1 weight percent of a catalyst having oxygen and the cation components in the proportions indicated by the empirical formula:

$$Bi_aV_bL_lM_mT_tO_x, \qquad \text{formula (1)}$$

wherein
L is one or more of K, Cs, Rb and Tl;
M is one or more of Mo, W, Cr, Ge, Sb, Sn, P, Pb and B;
T is one or more of Zn, Nb, Ta, Fe, Co, Ni Cu, Mn, Ti and rare earths;
a=1–25
b=1–50
l=0–1, usually 0–0.2
m=0.1–20
t=0–20
x is determined by the oxidation state of the other elements in the catalyst,
(a+b):(l+m+t)=20:1 to 1:5
a:b=1:5–5:1, usually 1:3–3:1,
with the proviso that the atomic ratio of Mo:V is zero to <10; said second catalyst composition being 0–99 weight percent of a diluent/support and 100–1 weight percent of a catalyst having oxygen and the cation components in the proportions indicated by the empirical formula:

$$Bi_nCe_pD_dE_eF_fMo_{12}W_gV_vO_y \qquad \text{formula (2)}$$

where

D is one or more of Fe, Mn, Pb, Co, Ni, Cu, Sn, P, Cr, Y, Mg, Ca, Sr, Ba and rare earths other than Ce and Sm;

E is one or more of Sb, Ge, As, Se, and Te;

F is one or more of an alkali metal, Tl, Ag and Sm and where n is 0.01–24, p is 0.01–24; (n+p) is 0.1–24, d is 0–10, e is 0–10, f is 0–6, g is 0–8, v is 0–0.5 and y is determined by the oxidation is 0–6, g is 0–8, v is 0–0.5 and y is determined by the oxidation state of the other elements present, wherein the weight ratio in said mixture of said first catalyst composition to said second catalyst composition is in the range of 0.001 to 2.5.

By "particulate mixture" as used herein is meant a mixture of solid particles or subdivided pieces of the first catalyst composition with separate and distinct solid particles of the second catalyst composition. The particles are often of a size used in fluidized bed reactors, say about 40 to 90 microns, but of course larger particles of catalyst can be employed for use in fixed or gravity flowing catalyst beds.

"Rare earths" as used herein means atomic numbers 57 through 71.

In the present process in all its embodiments the ratio of $O_2$ to $NH_3$ fed to the reaction zone is usually in the range from 1 to 10 (more often 1–5) and the ratio of inert gaseous diluent to paraffin is usually in the range zero to 5 (more often zero to 3).

The diluent or support for either catalyst composition is a refractory metal oxide or mixture, such as silica, silica-alumina, etc.

In the usual practice of the present invention the catalyst support/diluent for the catalyst of formula (1) is not an oxide of an element named in formula (1). Further, in the usual practice of the invention the catalyst support/diluent for the catalyst of formula (2) is not an oxide of an element named in formula (2).

In the catalyst compositions of the invention the catalyst empirical formulas (1) and (2) do not, of course, connote any particular chemical compound, nor indicate whether the elements are present as a mixture of individual oxides or as a complex oxide or oxides, or what separate crystalline phases or solid solutions may be present. Similarly, the designation of certain oxides, such as "silica" or "alumina" or $SiO_2$ or $Al_2O_3$, as supports or diluents is merely in accordance with convention in the inorganic oxide catalyst art, and such designations refer to compounds often regarded as supports in the catalyst art. Such designations, however, do not mean that the element involved is actually present as a simple oxide. Indeed, such elements may at times be present as a complex oxide with one, more than one, or all of the elements in formula (1) or formula (2), which complex oxides form during the precipitation or agglomeration, drying and calcining process for preparing the catalyst composition.

The process of the invention is especially useful in the ammoxidation of propane or isobutane.

In the preparation of the catalyst compositions of formula (1) or formula (2) the metal oxides can be blended together or can be formed separately and then blended or formed separately or together in situ. A useful manner of incorporating promoter elements is by choosing a water-soluble salt of the promoter element, forming an aqueous solution of the salt, and mixing the solution with a solution or a suspension of the base elements or salts thereof. Optionally, the promoter elements may be incorporated by the use of soluble complex salts or compounds with the desired base elements which upon calcination will yield the desired ratio of the elements in the finished catalyst.

Bismuth may be introduced into the catalyst as an oxide or as any salt which upon calcination will yield the oxide. Most preferred are the water-soluble salts which are easily dispersible within the catalyst and which form stable oxides upon heat-treating. The most preferred salt for introducing bismuth is bismuth nitrate.

To introduce the molybdenum component any molybdenum oxide such as the dioxide, trioxide, pentoxide or sesquioxide may be used; more preferred is hydrolyzable or decomposable molybdenum salt such as molybdenum halide. A preferred starting material is ammonium heptamolybdate.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result, upon heating to a temperature within the range disclosed hereinafter, in the oxides of the instant catalyst.

These catalyst compositions can conveniently be prepared by slurry techniques wherein an aqueous slurry containing all of the elements in the objective catalyst is produced. In any event, a solution or slurry containing all of the elements of the catalyst is formed. This is followed by evaporation, drying and then calcining the product in a molecular oxygen-containing atmosphere, such as air, at from 350° to 700° or 750° C., usually 400° to 650° C. The length of the calcination period may range from 30 minutes to 12 hours, but satisfactory catalyst compositions are usually obtained by calcination at such temperatures for a period of from 1 to 5 hours. Until calcination the compositions are not catalysts but are merely precatalysts with little or no catalytic activity. Liquids other than water, such as $C_1$ to $C_8$ alcohols can also be used to form the precatalyst slurry.

In the ammoxidation of the present invention, the reaction is carried out in the gas phase by contacting a mixture of the paraffin, ammonia and molecular oxygen, and inert diluent, if any, conveniently in a fixed bed of the catalyst mixture, or a gravity flowing bed, a fluidized bed or a fast transport reactor mode.

Examples of inert diluents useful in the reaction are $N_2$, He, $CO_2$, $H_2O$ and Ar.

The reaction temperature range can vary from 350° to 700° C., but is usually 430° to 520° C. The latter temperature range is especially useful in the case of propane ammoxidation to acrylonitrile.

The average contact time can often be from 0.01 to 10 seconds, but is usually from 0.02 to 10 seconds, more usually from 0.1 to 5 seconds.

The pressure of the reaction usually ranges from 2 to 45 psia. Most often, pressure is somewhat above atmospheric.

The following examples of the invention are exemplary and should not be taken as in any way limiting.

EXAMPLE 1

Bismuth nitrate dissolved in dilute nitric acid was mixed with a solution containing ammonium metavanadate and ammonium heptamolybdate dissolved in hot water. Silica sol and alumina sol were added to this and the slurry was evaporated to dryness over a hot plate. The dry material was heat treated at 290° C./3 hrs, 425° C./3 hrs and 610° C./3 hrs. The composition of the catalyst was 50% $BiV_{0.7}Mo_{0.5}O_x + 25\%$ $SiO_2 + 25\%$ $Al_2O_3$.

EXAMPLE 2

A catalyst with the composition 50% $BiV_{0.7}Mo_{0.5}SbO_x + 25\%$ $SiO_2 + 25\%$ $Al_2O_3$ was prepared as described in Example 1, except that $Sb_2O_5$ sol was added to the ammonium metavanadate and ammonium heptamolybdate solution.

EXAMPLE 3

This catalyst with the composition of 50% $BiV_{0.7}Mo_{0.5}Cr_{0.5}O_x + 25\%$ $SiO_2 + 25\%$ $Al_2O_3$ was prepared as in Example 1 except that chromium nitrate dissolved in water was added to the bismuth nitrate solution.

EXAMPLE 4

This catalyst with the composition 50% $BiV_{0.7}Mo_{0.5}Cr_{0.5}O_x + 50\%$ $Al_2O_3$ was prepared as described in Example 3, except that no silica sol was used.

EXAMPLE 5

A solution containing chromium nitrate and bismuth nitrate dissolved in dilute nitric acid was mixed with a solution containing ammonium metavanadate and ammonium heptamolybdate dissolved in hot water. Silica sol and alumina sol were added to this and the slurry was evaporated to dryness over a hot plate. The dry material was heat treated at 290° C./3 hours, 425° C./3 hours, and 610° C./3 hours. The composition of the catalyst was 50% $BiV_{0.7}Mo_{0.5}CrO_x + 25\%$ $SiO_2 + 25\%$ $Al_2O_3$.

EXAMPLE 6

Ammonium metavanadate was dissolved in hot water and ammonium heptamolybdate was added, followed by $SnO_2$ sol. In a separate beaker, bismuth nitrate was dissolved in 10% nitric acid, and then chromium nitrate was added. This solution was added slowly to the V-Mo-Sn dispersion with stirring, Silica sol and then alumina sol were added to the resulting slurry. It was stirred and heated to remove excess $H_2O$, dried overnight at about 120° C., heated 3 hours at 290° C., 3 hours at 425° C., ground and screened to 20-35 mesh. A portion was then calcined at 610° C. for 3 hours. The composition was 50% $BiV_{0.7}MoCr_{0.5}Sn_{0.5}O_x + 25\%$ $SiO_2 + 25\%$ $Al_2O_3$.

EXAMPLE 7

Bismuth nitrate dissolved in dilute nitric acid was mixed with a solution containing ammonium metavanadate and ammonium heptamolybdate dissolved in hot water. Silica sol and alumina sol were added to this and the slurry was evaporated to near dryness over a hot plate. The dry material was heat treated at 290° C./3 hours, 425° C./3 hours, ground and screened to 20-35 mesh and heated at 610° C./3 hours. The composition of the catalyst was 50% $BiV_{0.7}MoO_x + 25\%$ $SiO_2 + 25\%$ $Al_2O_3$.

EXAMPLE 8

This catalyst with the composition 50% $BiV_{0.7}Mo_{0.5}W_{0.5}O_x + 25\%$ $SiO_2 + 25\%$ $Al_2O_3$ was prepared as described in Example 1, except that ammonium metatungstate was included in the second solution.

EXAMPLE 9

A solution containing bismuth nitrate dissolved in dilute nitric acid was mixed slowly with stirring with a solution containing ammonium metavanadate, ammonium heptamolybdate and ammonium metatungstate dissolved in hot water. Silica sol and alumina sol were added to this and the slurry was evaporated to near dryness over a hot plate, and dried overnight at 120° C. The dry material was heat treated at 290° C./3 hours, 425° C./3 hours, ground and screened to 20-35 mesh and calcined at 610° C./3 hours. The composition of the catalyst was 50% $BiV_{0.7}Mo_{0.3}W_{0.5}O_x + 25\%$ $SiO_2 + 25\%$ $Al_2O_3$.

EXAMPLE 10

A catalyst having the empirical composition 50 wt % $Bi_4Ce_4Mo_{10}W_2O_x + 50$ wt % $SiO_2$ was made as follows:
1765.65 g of $(NH_4)_6Mo_7O_{24} \cdot 4 H_2O$ were dissolved in 2000 ml warm water. 545.7 g $(NH_4)_6H_2W_{12}O_{40} \cdot H_2O$ — 85% $WO_3$—were dissolved with the addition of more $H_2O$, to make a solution of 4750 ml. A 40 wt % $SiO_2$ sol ($NH_4^+$ stabilized) was added in the amount of 8728.75 g.

In a separate beaker, 1940.4 g $Bi(NO_3)_3 \cdot 5 H_2O$ were dissolved in a mixture of 47.5 ml conc. $HNO_3$ and 250 ml $H_2O$. 2193.04 g $(NH_4)_2Ce(NO_3)_6$ were then dissolved in the solution. The resulting solution was added slowly with stirring to the molybdate tungstate silica solution. The pH of the resulting slurry was adjusted to about 3 by the addition of about 1500 ml of concentrated ammonium hydroxide. A portion of this slurry was then heated and stirred to remove excess water. It was dried overnight at 110° C.

The dried material was denitrified by heating at 290° C. or 3 hours and then at 425° C. for 3 hours. It was ground and screened to between 20-35 mesh particle size. Final calcination was at 650° C. for 3 hours.

In the ammoxidation runs of the following examples summarized in Table 1, the mixture of catalysts is in a tubular ⅜ inch I.D. stainless steel fixed bed reactor. To make the mixture of particulate catalysts, the desired weight of each of the two catalyst compositions is put in a vial and shaken until uniformly dispersed before placing the desired amount of the catalyst mixture in the reaction tube. The reactor is equipped with a preheat leg and is immersed in a temperature controlled molten salt bath. The gaseous feed components are metered through mass flow controllers into the bottom of the reactor through the preheat leg. Water is introduced through a septum at the top of the preheat leg, using a syringe pump. The feed is fed to the catalyst for a pre-run of 1 hour before collection of product unless a longer pre-run time is noted; the runs of each example last 30-60 minutes during which the product is collected for analysis.

EXAMPLE 11

In this example the gaseous feed components were metered through mass flow controllers into the bottom of the reactor through the preheat leg. The catalyst was a mixture of the catalyst of Example 1 and the catalyst of Example 10 in the weight ratio of the former to the latter of 1.0. Water was introduced through a septum at the top of the preheat leg, using a syringe pump. The reaction temperature was 470° C. and the molar feed ratios were 5 propane/$1NH_3/2O_2/1H_2O$. The contact time was 1.4 seconds. Analysis of the reactor effluent showed that propane conversion was 12.2 percent; yield and selectivity of propane to acrylonitrile were 6.3 and 51.6 percent, respectively.

EXAMPLE 12

In this example the gaseous feed components were metered through mass flow controllers into the bottom of the reactor through the preheat leg. The catalyst was a mixture of the catalyst of Example 2 and the catalyst of Example 10 in the weight ratio of the former to the latter of 0.36. Water was introduced through a septum at the top of the preheat leg, using a syringe pump. The reaction temperature was 470° C. and the molar feed ratios were 5 propane/1NH$_3$/2O$_2$/1H$_2$O. The contact time was 2.0 seconds. Analysis of the reactor effluent showed that propane conversion was 11.6 percent; yield and selectivity of propane to acrylonitrile were 6.6 and 56.9 percent, respectively.

EXAMPLE 13

In this example the gaseous feed components were metered through mass flow controllers into the bottom of the reactor through the preheat leg. The catalyst was a mixture of the catalyst of Example 4 and the catalyst of Example 10 in the weight ratio of the former to the latter of 0.11. Water was introduced through a septum at the top of the preheat leg, using a syringe pump. The reaction temperature was 470° C. and the molar feed ratios were 5 propane/1NH$_3$/2O$_2$/1H$_2$O. The contact time was 1.7 seconds. Analysis of the reactor effluent showed that propane conversion was 11.8 percent; yield and selectivity of propane to acrylonitrile were 6.4 and 54.1 percent, respectively.

EXAMPLE 14

In this example the gaseous feed components were metered through mass flow controllers into the bottom of the reactor through the preheat leg. The catalyst was a mixture of the catalyst of Example 3 and the catalyst of Example 10 in the weight ratio of the former to the latter of 0.15. Water was introduced through a septum at the top of the preheat leg, using a syringe pump. The reaction temperature was 470° C. and the molar feed ratios were 5 propane/1NH$_3$/2O$_2$/1H$_2$O. The contact time was 1.8 seconds. Analysis of the reactor effluent showed that propane conversion was 10.6 percent; yield and selectivity of propane to acrylonitrile were 6.1 and 57.3 percent, respectively.

EXAMPLE 15

In this example the gaseous feed components were metered through mass flow controllers into the bottom of the reactor through the preheat leg. The catalyst was a mixture of the catalyst of Example 5 and the catalyst of Example 10 in the weight ratio of the former to the latter of 0.15. Water was introduced through a septum at the top of the preheat leg, using a syringe pump. The reaction temperature was 470° C. and the molar feed ratios were 5 propane/1NH$_3$/2O$_2$1H$_2$O. The contact time was 1.8 seconds. Analysis of the reactor effluent showed that propane conversion was 12.3 percent; yield and selectivity of propane to acrylonitrile were and 7.3 and 58.9 percent, respectively.

EXAMPLE 16

In this example the gaseous feed components were metered through mass flow controllers into the bottom of the reactor through the preheat leg. The catalyst was a mixture of the catalyst of Example 6 and the catalyst of Example 10 in the weight ratio of the former to the latter of 0.11. Water was introduced through a septum at the top of the preheat leg, using a syringe pump. The reaction temperature was 470° C. and the molar feed ratios were 5 propane/1NH$_3$/2O$_2$/1H$_2$O. The contact time was 1.5 seconds. Analysis of the reactor effluent showed that propane conversion was 11.6 percent; yield and selectivity of propane to acrylonitrile were 6.5 and 56.2 percent, respectively.

EXAMPLE 17

In this example the gaseous feed components were metered through mass flow controllers into the bottom of the reactor through the preheat leg. The catalyst was a mixture of the catalyst of Example 9 and the catalyst of Example 10 in the weight ratio of the former to the latter of 0.15. Water was introduced through a septum at the top of the preheat leg, using a syringe pump. The reaction temperature was 470° C. and the molar feed ratios were 5 propane/1NH$_3$/2O$_2$/1H$_2$O. The contact time was 1.8 seconds. Analysis of the reactor effluent showed that propane conversion was 7.8 percent; yield and selectivity of propane to acrylonitrile were 4.6 and 58.8 percent, respectively.

EXAMPLE 18

In this example the gaseous feed components were metered through mass flow controllers into the bottom of the reactor through the preheat leg. The catalyst was a mixture of the catalyst of Example 8 and the catalyst of Example 10 in the weight ratio of the former to the latter of 0.45. Water was introduced through a septum at the top of the preheat leg, using a syringe pump. The reaction temperature was 470° C. and the molar feed ratios were 5 propane/1NH$_3$/2O$_2$/1H$_2$O. The contact time was 2.1 seconds. Analysis of the reactor effluent showed that propane conversion was 11.7 percent; yield and selectivity of propane to acrylonitrile were 7.0 and 60.0 percent, respectively.

EXAMPLE 19

In this example the gaseous feed components were metered through mass flow controllers into the bottom of the reactor through the preheat leg. The catalyst was a mixture of the catalyst of Example 7 and the catalyst of Example 10 in the weight ratio of the former to the latter of 1.0. Water was introduced through a septum at the top of the preheat leg, using a syringe pump. The reaction temperature was 470° C. and the molar feed ratios were 5 propane/1NH$_3$/2O$_2$/1H$_2$O. The contact time was 1.4 seconds. Analysis of the reactor effluent showed that propane conversion was 11.6 percent; yield and selectivity of propane to acrylonitrile were 5.9 and 50.9 percent, respectively.

EXAMPLE 20

This catalyst with the composition 50% BiV$_{0.7}$W$_{0.5}$O$_x$+25% SiO$_2$+25% Al$_2$O$_3$ was prepared as described in Example 1, except that ammonium metatungstate was used instead of ammonium heptamolybdate.

EXAMPLE 21

In this example the gaseous feed components were metered through mass flow controllers into the bottom of the reactor through the preheat leg. The catalyst was a mixture of the catalyst of Example 20 and the catalyst of Example 10 in the weight ratio of the former to the latter of 0.15. Water was introduced through a septum at the top of the preheat leg, using a syringe pump. The reaction temperature was 470° C. and the molar feed ratios were 5 propane/1NH$_3$/2O$_2$/1H$_2$O. The contact time was 1.9 seconds. Analysis of the reactor effluent showed that propane conversion was 7.4 percent; yield and selectivity of propane to acrylonitrile were 4.1 and 54.8 percent, respectively.

As will be evident to those skilled in the art various modifications of this invention can be made or followed in the light of the foregoing disclosure and discussion without departing from the spirit and scope of the disclosure or from the scope of the claims.

We claim:

1. A process for the ammoxidation of a C$_3$ to C$_5$ paraffin to an $\alpha,\beta$-unsaturated mononitrile which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:NH$_3$ in the range from 2 to 16, and a mole ratio of paraffin:O$_2$ in the range from 1 to 10 said first catalyst composition being 0-99 weight percent of a diluent/support and 100-1 weight percent of a catalyst having oxygen and the cation components in the proportions indicated by the empirical formula:

$$Bi_aV_bL_lM_mT_tO_x, \qquad \text{formula (1)}$$

wherein

L is one or more of K, Cs, Rb and Tl;

M is one or more of Mo, W, Cr, Ge, Sb, Sn, P, Pb and B;

T is one or more of Zn, Nb, Ta, Fe, Co, Ni Cu, Mn, Ti and rare earths, a=1-25
b=1-50
l=0-1
m=0.1-20
t=0-20 x is determined by the oxidation state of the other elements in the catalyst, $(a+b):(l+m+t)=20:1$ to 1:5
a:b=1:5-5:1 with the proviso that the atomic ratio of Mo:V is zero to <10; said second catalyst composition being 0-99 weight percent of a diluent/support and 100-1 weight percent of a catalyst having oxygen and the cation components in the proportions indicated by the empirical formula:

$$Bi_nCe_pD_dE_eF_fMo_{12}W_gV_vO_y \qquad \text{formula (2)}$$

where

D is one or more of Fe, Mn, Pb, Co, Ni, Cu, Sn, P, Cr, Y, Mg, Ca, Sr, Ba and rare earths other than Ce and Sm;

E is one or more of Sb, Ge, As, Se, and Te;

F is one or more of an alkali metal, Tl, Ag and Sm and where n is 0.01-24, p is 0.01-24; (n+p) is 0.1-24, d is 0-10, e is 0-10, f is 0-6, g is 0-8, v is 0-0.5 and y is determined by the oxidation state of the other elements present, wherein the weight ratio in said mixture of said first catalyst composition to said second catalyst composition is in the range of 0.001 to 2.5.

2. A process of claim 1 wherein said mole ratio of paraffin:NH$_3$ is in the range from 3 to 7.

3. A process of claim 1 wherein said mole ratio of paraffins:O$_2$ is in the range from 1.5 to 5.

4. A process of claim 2 wherein said mole ratio of paraffin:O$_2$ is in the range from 1.5 to 5.

5. A process according to claim 1 wherein the mole ratio of O$_2$ to NH$_3$ in the feed to the reaction zone is in the range from 1 to 10.

6. A process according to claim 1 wherein the mole ratio of inert gaseous diluent to paraffin in the feed to the reaction zone is in the range from zero to 5.

7. A process of claim 1 wherein said paraffin is propane or isobutane.

8. A process of claim 1 wherein said paraffin is propane.

9. A process of claim 2 wherein said paraffin is propane or isobutane.

10. A process of claim 4 wherein said paraffin is propane.

* * * * *